United States Patent [19]

Regen

[11] Patent Number: 4,594,193

[45] Date of Patent: Jun. 10, 1986

[54] THIOL BASED LIPIDS AND MEMBRANES MADE THEREFROM

[75] Inventor: Steven L. Regen, Milwaukee, Wis.

[73] Assignee: Research Corporation, New York, N.Y.

[21] Appl. No.: 654,831

[22] Filed: Sep. 26, 1984

[51] Int. Cl.[4] ................................................. C07F 9/10
[52] U.S. Cl. ................................... 260/399; 260/402.5
[58] Field of Search ............. 260/399, 925, 945, 402.5

[56] References Cited

PUBLICATIONS

Regen et al, *Journal of the American Chemical Society*, vol. 105, No. 20, Oct. 5, 1983, pp. 6354–6355.
Brunner et al, *The Journal of Biological Chemistry*, vol. 255, No. 8, Apr. 25, 1980, pp. 3320–3329.

*Primary Examiner*—Charles F. Warren
*Assistant Examiner*—Elizabeth A. Flaherty
*Attorney, Agent, or Firm*—Scully, Scott, Murphy & Presser

[57] ABSTRACT

Thiol containing lipids as provided which are used to construct polymerizable-deplymerizable vesicles that may be used as slow release in vivo medication delivery systems.

24 Claims, No Drawings

THIOL BASED LIPIDS AND MEMBRANES MADE THEREFROM

The subject matter of this patent application was the result of work done under PHS Contract No. CA 28891 sponsored by the National Cancer Institute, U.S. Department of Health, Education and Welfare, and The National Science Foundation, under Grant CHE-8401473.

BACKGROUND OF THE INVENTION

Bilayer vesicles or liposomes whose walls comprise monomeric lipids, such as phosphatidyl cholines, have been studied as drug carriers, offering the attractive properties of promoting passage of the drugs across cell membranes, increasing drug lifetime in the plasma and retarding drug catabolism. Liposomes formed from monomeric phosphatidyl cholines are, however, thermodynamically and biologically unstable and the rate of leakage of entrapped drugs from them is relatively high. Consequently, their practical utility for such purposes may be limited.

More recently, the concept of polymerized vesicles, formed from polymerizable material has been proposed (Regen et al., *J. Am. Chem. Soc.* 1980, 102, 6638) as a method of achieving enhanced stability. Vesicles of this type are also disclosed in U.S. patent application Ser. No. 618,634 filed June 8, 1984 as a division of Ser. No. 382,296 filed May 26, 1982 which was a continuation-in-part of Ser. No. 280,633 filed July 6, 1981. Biological studies conducted to date on such polymerized vesicles, such as vesicles derived from bis[12-(methacryloyloxy)-dodecanoyl]-L-alpha-phosphatidyl-choline, indicate that they do not induce platlet aggregation to any appreciable degree and can be administered in substantial amounts, intravenously, without any evidence of acute toxicity, as indicated by survival, kidney function and liver function. However, chronic parenteral use of these as well as all other previously reported polymerized phosphatidylcholine vesicles may result in tissue accumulation of the nondegradable polymeric backbones.

U.S. Pat. No. 4,348,329 discloses conjugated di-yne containing phospholipids which may be polymerized and/or crosslinked, but not reversibly so.

Thus, the use of polymerized vesicles for the controlled, in vivo delivery of medicaments may require, in some cases, the need for vesicles that, in one way or another, could be safely removed or prevented from accumulating, as such.

An object of the present invention therefore, is to provide a novel class of monomeric materials from which polymerized biodegradable vesicles may be prepared.

A further object of the present invention is to provide polymeric biodegradable vesicles.

A further object of the present invention is to provide a novel class of polymeric vesicles which will provide a polymerized liposome network which may be readily depolymerized.

SUMMARY OF THE INVENTION

It has now been found that the objects of the present invention can be achieved by forming vesicles from novel polymerizable lipid compounds containing mercaptan groups. These SH containing lipid compounds are themselves prepared from novel disulfide group containing lipid compounds. The mercaptan group containing lipid compounds may be linearly polymerized through mercaptan groups on different molecules of the compounds. The resulting disulfide containing polymers, may be readily depolymerized, and, as such, are believed to the more susceptible to biodegradation at such disulfide links.

DESCRIPTION OF THE PREFERRED EMBODIMENT

The polymerizable mercaptan containing lipid compounds of the present invention include those having the following structure:

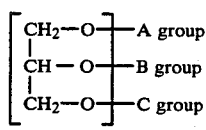   I wherein one of the A, B and C groups is a head group and one or two of the remaining of such A, B and C groups have the structure

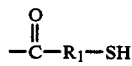   II wherein $R_1$ is a saturated or unsaturated $C_{10}$ to $C_{25}$ hydrocarbon radical which may be alkyl, alkenyl, aryl, alkaryl, or aralkyl. The $R_1$ alkyl or alkenyl groups may be linear, branched or cyclic. The SH group can be located anywhere on the $R_1$ group. The preferred $R_1$ groups are $C_{10}$ to $C_{25}$ linear or branched alkyl or alkenyl groups such as $(CH_2)_n$ and $CH-(CH_2)_n-CH_3$ wherein n is about 10 to 20. The more preferred of the I structure compounds are those containing two structure II groups such as

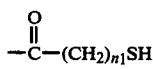   III wherein $n_1$ is about 10 to 25
and

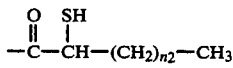   IV wherein $n_2$ is about 9 to 25.

Where the I structure compounds contain only one structure II group (and one head group) the remaining A, B or C group would be an inert group such as one of the structure

   V wherein $R_2$ is a $C_9$ to $C_{25}$ saturated or unsaturated hydrocarbon radical which may be alkyl, alkenyl, aryl, alkaryl or aralkyl.

The head groups which are used in the structure I compounds are groups which are liposome forming groups which are adaptable to forming vesicles.

Such groups would include phosphatidyl choline type groups, such as those having the structure

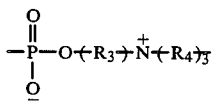  VI wherein $R_3$ and $R_4$ are saturated or unsaturated hydrocarbon radicals having 1 to about 4 Carbon atoms. $R_4$ is preferably alkyl, such as methyl and ethyl, and $R_3$ is preferably $(CH_2)_{n_3}$ wherein $n_3$ is about 2 to 4.

The head groups used are those that would be inert in all the reactions discussed herein wherein the head group containing compounds are employed.

When the I compounds are polymerized, in accordance with the present invention, disulfide formation occurs intermolecularly, rather than intramolecularly. When the I compounds which contain two SH groups polymerize they form linear polymers having a degree of polymerization (DP) of at least 17 to 25 and preferably of more than 25.

When the I compounds which contain only one SH group are oxidized they form dimers with each other. Alternatively they may also be used to terminate polymers formed from I compounds having two SH groups.

Both the dimers and the linear polymers, capped or uncapped, can be readily polymerized (switched on) and depolymerized (switched off) via a thiol-disulfide redox cycle. The dimers and polymers may also be formed by direct UV irradiation at 254 nm for about 30 to 60 minutes or by oxidation with excess $H_2O_2$ at about $40 \pm 10°$ C.

The polymerizable mercaptan containing lipid compounds of the present invention are formed from disulfide compounds including those having the following structure:

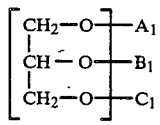  VII wherein one of the $A_1$, $B_1$ and $C_1$ groups is a head group and one or two of the two remaining of such $A_1$, $B_1$ and $C_1$ groups have the structure $$-\overset{O}{\overset{\|}{C}}-R_1-SS-X$$  VIII wherein $R_1$ is as defined above and X is an inert radical such as a $C_1$ to $C_{25}$ hydrocarbon radical such as alkyl, alkenyl, aryl, alkenyl or aralkyl. X is preferably an $R_1$ group and most preferably a $C_1$ to $C_4$ alkyl radical. The —SS—X group can be located anywhere on the $R_1$ group.

Where the VII structure compounds contain only one structure VIII (and one head group) the remaining $A_1$, $B_1$ or $C_1$ group would be an inert group such as a structure V group.

The preferred structure VII compounds are those which contain two structure VIII groups such as

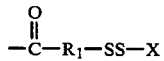  IX and

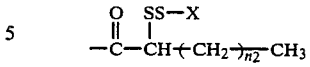  X wherein $n_1$ and $n_2$ are as defined above and the structure VII compounds containing such structures IX and X are the precursors of the compounds of structure I which contain structures III and IV, respectively.

The mercaptan containing lipid compounds of structure I are formed by reduction of the disulfide compounds of structure VII under the following general reaction scheme A:

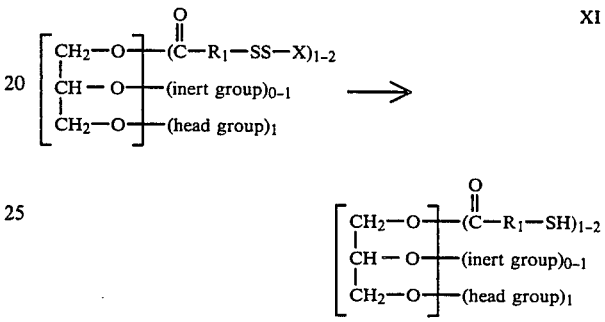

This reaction A may be conducted at room temperature range of about 25° C. to 40° C., at atmospheric pressure, in a solvent mixture of ethyl alcohol and water and with tributyl phosphine as a reducing agent. The disulfide containing lipid compounds of structure VII are formed from a glycerol derivative containing the head group and a disulfide compound of the structure $$X-SS-R_1-COOH$$  XII wherein $R_1$ and X are as defined above, and, optionally, a source of an inert group of structure V.

The preferred of the structure XII compounds have the structures

  XIII and

  XIV wherein X, $n_1$ and $n_2$ are as defined above.

The XIII and XIV structure compounds are used as precursors, with the source of a head group, and, optionally, a source of an inert structure V group, of the structure VII compounds containing groups of structure IX and X, respectively.

The sources of the inert groups of structure V would be commercially available fatty acids of suitable, $C_{10}$ to $C_{26}$, chain lengths.

Where the head group is to be a phosphoryl-choline group a preferred source of said head group is sn-glycero-3-phosphorylcholine (GPC) converted as a $CdCl_2$ complex (GPC—$CdCl_2$).

Thus the disulfide containing lipid compounds of structure VII are formed, using GPC—$CdCl_2$ as a source of a head group and dicyclohexyl-carbodiimide (DCC) as follows:

B reaction:

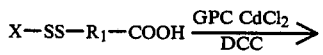

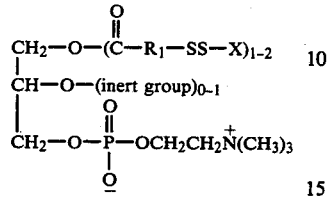

Other types of head groups that might be synthesized would be derivative phospholipids such as phosphatidyl alkanol amine such as phosphatidyl ethanol amine and phosphatidyl glycerol. These compounds are readily accessible through standard enzymatic exchange using phospholipase D. Pharmaceutically acceptable salts of the head groups may also be used.

Reaction B may be conducted at a temperature of about 25° to 40° C. at atmospheric pressure and in a solvent such as dichloromethane (methylene chloride) or trichloromethane (chloroform).

The disulfide compounds of structure XII are formed by reacting, in a Reaction C, a compound of the structure

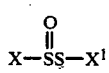      XVI wherein $R_1$ is as defined above with a compound of the structure

      XVII wherein X is as defined above and $X^1$ is an aliphatic $C_2$ to $C_5$ hydrocarbon radical.

The following are the most preferred of the monomeric compounds according to the present invention:

Structure XVII:

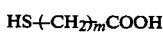

Structure XVI:

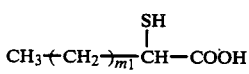      XVIA wherein m is about 10 to 25 and preferably is 10 and 15, and

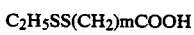      XVIB wherein $m_1$ is about 8 to 23 and preferably is 10 to 15.

Structure XII:

$C_2H_5SS(CH_2)mCOOH$      XIIA and

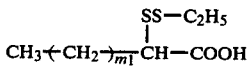      XIIB wherein m and $m_1$ are as defined above.

Structure VII:

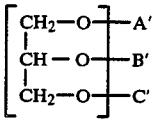      VIIA wherein A' and B' are each

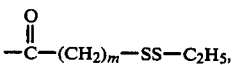

wherein m is as defined and C' is as defined below; and

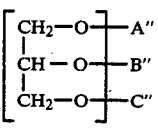      VIIB wherein A'' and B'' are each

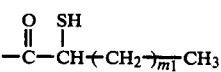

and wherein $m_1$ is as defined above, and C'' is as defined below

Structure I:

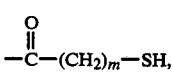      IA wherein A''' and B''' are each

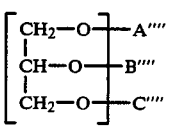

m is as defined above and C''' is as defined below and

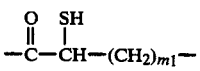      IB wherein A'''' and B'''' are each $$-\overset{O}{\underset{\|}{C}}-\overset{SH}{\underset{|}{CH}}-(CH_2)_{m_1}-$$

$CH_3$, $m_1$ is as defined above and C'''' is as defined below.

In each of such preferred structures, C', C", C''' and C'''' is

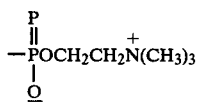

Where the mercaptan containing lipids of Structure I which contain two mercaptan groups are polymerized the resulting polymer has the following structure:

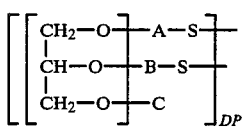  XVIII wherein A-S and B-S correspond to the mercaptan containing A and B groups of Structure I, minus a hydrogen atom at the original site of the SH radical, and DP is a whole number of about 17 to 25 and C is a head group as defined above.

Where the mercaptan containing lipids of Structure I which contain only one mercaptan group are dimerized the resulting dimer has the following structure

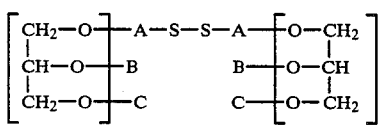  XIX wherein the —A—S—S—A— group forms from two mercaptan containing A groups of Structure I, with the loss of two hydrogen atoms from the original sites of the SH radicals, B in an inert group as defined above and C is a head group as defined above.

The disulfide linkages in the polymers of Structure XVIII and in the dimers of structure XIX can be readily split to depolymerize such compounds by the use of a reducing agent such as dithiothreitol, trialkylphosphines in water and mercaptoethanol, at atmospheric pressure and at a temperature of about 25° to 50° C.

In forming the polymers of Structure XVIII and/or the dimers of Structure XIX, the lipid monomers of Structure I which are used for such purposes may comprise either a polymerizable/dimerable charge of lipids all of which have the exact same structure, or the charge can comprise a mixture of lipids having different structures, ie, different A, B and/or C groups.

Where the lipid of Structure I which contains only one mercaptan group is used to cap or chain terminate a polymer of Structure XVIII, the two terminal groups of the capped polymer will have the structure of Structure XIX.

The dimers of the present invention would have utility as vesicle components to help stabilize other monomeric vesicles. The endcapping of the polymers of structure XVIII would be useful when precise control of the molecular weight of the capped polymer is desired. The molecular weight is likely to control diffusion rates out of these vesicles, i.e., the time-release activity of the vesicles.

Polymerized Vesicle Utility

The motivation for the construction of the polymerized—depolymerized liposomal networks of the present invention has been, at least, twofold. First, reversibly polymerized vesicles constitute unique highly flexible biomembrane models. In the polymerized state (the "on position"), lateral diffusion within the bilayer can be significantly reduced or eliminated; and in the depolymerized mode (the "off position"), lateral diffusion can be restored. One area where such membranes can prove particularly useful is in the field of immunochemistry. The lateral mobility and distribution of membrane antigens/haptens is believed to play an important role in the immune response. In principle, the polymerized (or partially polymerized)—depolymerized vesicles can be used to fine-tune the lateral motion of haptens, to hold them in place, and to release them at will. Furthermore, the ability to depolymerize a vesicle network would allow one to take apart and recover key membrane components.

A second reason for preparing reversibly polymerized vesicles relates to their potential biodegradability and utility as drug carriers. Polymerized phospholipid vesicles have been suggested for use in drug delivery. S. L. Regen et al. J. Amer.Chem. Soc. 1980, Vol. 102, page 6638 et seq; S. L. Regen et al. J. Amer. Chem soc., 1982, Vol. 104, page 791 et seq; L. Gros et al. Angew. Chem., Int. Ed. Engl. 1981, Vol. 20, page 305 et seq; J. H. Fendler et al., Acc. Chem Res. 1984, Vol. 17 page 3 et seq; and S. L. Regen, Ann. N.Y. Acad. Sci, 1984. It is significant to note, however, that all the polymerized liposomes that have thus been reported so far possess nonbiodegradable all-carbon backbones. Polymerized vesicles that are susceptible to depolymerization in vivo are clearly more desirable for this end use.

Model Example of Preparation of Polymerizable Vesicle

A compound of Structure IA having the structure

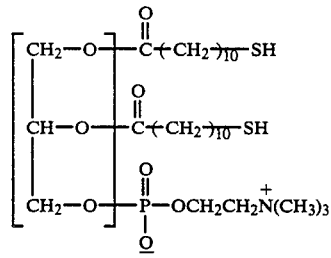  XX was prepared as follows:

In a Reaction C, 11-mercapoundecanoic acid (XVIA) was reacted with ethyl ethane thiosulfate (XVII) in chloroform to produce an 80% isolated yield of 11-ethyldithioundecanoic acid (XIII wherein $n_1$ is 10). Subsequent esterification of this XIII compound, in a Reaction B, with sn-glycero-3-phosphocholine-CdCl$_2$ (GPC-CdCl$_2$) furnished a 91% isolated yield of 1,2-bis [11(ethyldithio)undecanoyl-sn-glycero-3-phosphocholine (VIIA, wherein m is 10). The reduction of this VII A compound in a Reaction A with tributylphosphine in a 1:1 admixture of ethanol and water produced a 95% isolated yield of the Structure XX compound. Other Structure IA compounds made with a phosphocholine head group were made using such sequence of reaction steps. Thus, starting with 16-mercapto-palmitic acid as the compound of Structure XVIA, a compound XXI of Structure IA, wherein m is 15, was prepared. Further, starting with 1-mercapto-palmitic acid as the compound of Structure XVIB, a compound XXII of Structure IB, wherein m is 13, was prepared.

General Procedure for Forming Vesicles

Vesicles derived from the lipid compounds such as XX, XXI, and XXII were prepared by (a) coating the lipid onto the walls of a round-bottomed flask from a chloroform solution thereof and then evaporating the chloroform, (b) dispersing the lipid into a 10 mM borate buffer (pH 8.5) containing 140 mM NaCl and 2 mM $NaN_3$ (vortex mixing), and (c) irradiating the dispersion with ultrasound at 50° C. under a nitrogen atmosphere to constant turbidity. Thin-layer chromatography plus thiol analysis indicated that no lipid decomposition occurred during sonication. Opalescent to optically clear aqueous dispersions were obtained in all cases. Vesicles formed from XXI exhibited the poorest stability, precipitating on standing after a few ours at room temperature. Gel filtration of dispersions of XX and XXII using a Sepharose 6B column resulted in a 96 and 90% vescile recovery in the void volume, respectively (based on phosphorous analysis). Vesicles of XXI proved to be too unstable to survive similar Gel filtration. The greater inherent stability of vesicles formed from XX relative to vesicles formed from XXI is surprising in view of the shortness of the aliphatic chains of XX.

Despite the relative instability of the vesicles formed from the XXI lipids such vesicles/lipids would still have utility as drug carriers since they would still be stable enough in the polymerized state to be reasonably useful for this purpose.

General Polymerization of the Vesicles

Oxidative polymerization of all the vesicle dispersions was carried out by treatment with excess $H_2O_2$ at 40° C. for about four hours. Qualitative thin-layer chromatography showed in each case of single spot at the origin. In order to establish that interlipid oxidative coupling had occurred, an authentic sample of a cyclic monomer, XXIII, was synthesized, via oxidation of XX with iodine in benzene under high dilution conditions. The monomeric nature of this Structure XXIII product was confirmed by fast atom bombardment mass spectrometry which showed a parent ion at MH+ m/z=656. No evidence for dimer formation was found. Migration of XXIII on silica gel was very similar to that of its thiol precursor [$R_f$=0.26 (XX); $R_f$=0.30 (XXIII); silica, $CHCl_3/CH_3OH/H_2O$ (65/25/4)]. A qualitative analysis (Ellman test) also confirmed the absence of thiol groups. The lack of migration of oxidized XXI and XXII (aqueous dispersions) from the origin on silica gel is, therefore, taken as positive evidence for dominant interlipid coupling.

The compound of Structure XXIII had the following structure:

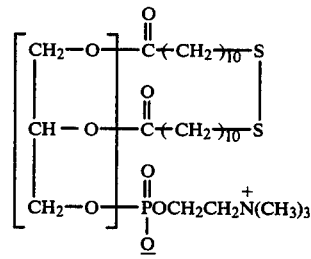

In more generic form the cyclic compounds of the present invention would have the following structures

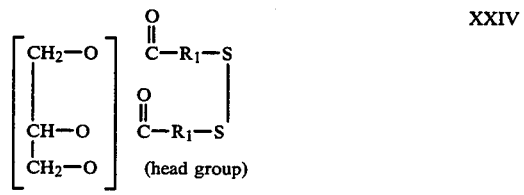

wherein $R_1$ and (head group) are as defined above.

The disulfide linkages of the XXIV Structure compounds will form when the mercaptan groups from which they are formed are positioned either at the terminal position of the $R_1$ group, or at any intermediate point in the $R_1$ group. The tendency of the disulfide groups to form increases as the mercaptan groups are positioned, on their respective $R_1$ groups, closer together.

In addition to their utility as analytical tools as disclosed above, the XXIV compounds would also have utility as vesicle forming reagents. When reacted with catalytic amounts of dithiothreitol, the disulfide groups are disproportionated, it is believed, by trace thiol groups that are formed during the initiation step of the reaction, and polymerized vesicles are subsequently formed.

Additional Properties of the Polymerized Vesicles

The turbidity of all dispersions, measured as the apparent absorbance at 400 nm, changed by less than 7% after oxidation. Thiol analysis showed that extensive oxidation had occurred (See Table I). Analysis of polymerized XX (obtained from a vesicle dispersion after lyphophilization) in $CD_3OD$ by $^1H$ HMR (250 MHz) indicated a ratio of $CH_2S/CH_2CO=1.0$. No signals were observed in the region expected for methylene protons alpha to sulfoxide or sulfone groups (i.e., S=2.7 to 3.2). Overoxidation of the disulfide moiety, therefore, does not appear to proceed to any significant degree under the reaction conditions used.

Gel filtration (Sepharose 6B) of polymerized aqueous dispersions of XX, and XXII afforded a vesicle recovery of 90 and 95%, respectively, in the void volume of the column. In the polymerized state, vesicles derived from XXI exhibited substantially improved stability and could be recovered in the void volume (85%) of a Sepharose 6B column. Electron microscopic examination of polymerized dispersions of XX, XXI and XXII confirmed the presence of closed spheres. The average diameter of the polymerized vesicles derived from XX and XXII was about 200 Å; polymerized vesicles formed from XXI had an average diameter of about 300

Å. Based on the data obtained to date it would be expected that polymerized vesicles could be made with an average diameter of about 200 to 1000 Å, and preferably from about 200 to 400 Å. (Å=angstrom unit)

TABLE I
Properties of Oxidatively Polymerized Phospholipid Vesicles

| Initial Monomer Composition[a] of Structure | Thiol Content Remaining (%)[b] | $\overline{X}_n$ | $\overline{M}_n$ |
|---|---|---|---|
| XX | 4 | 25 | 16,450 |
| XXI | 6 | 17 | 13,300 |
| XXII | 5 | 20 | 15,960 |

[a]Oxidation was carried out at pH 8.5 using about 1.5 mg of phospholipid/mL and 20 equivalents of 30% $H_2O_2$ for 4 hours at 40° C. In all cases the change in turbidity after oxidation was less than 7%.
[b]The thiol/phosphorous ratio, determined for dispersion of XX, XXI and XXII before oxidation ranged between 1.6 and 1.8. The percentage of remaining thiol groups was determined using the phophorous analysis as an internal reference.

Degree of Polymerization Within the Bilayer

If it is assumed that intramolecular coupling is negligible within the vesicle bilayers, reasonable estimates of the number average degree of polymerization, $\overline{X}_n$, and the number average molecular weight, $\overline{M}_n$, can be made using equations D and E (A. Rudin, "The Elements of Polymer Science and Engineering", Academic Press, New York, 1982, page 171 et seq.) Here, p=the extent of conversion (as determined by the remaining thiol content) and $M_o$ is the molecular weight of the lipid monomer. Thus, in the oxidized state, vesicles of XX, XXI, and XXII contain an average of about 25, 17, and 20 lipids per polymer chain, respectively (Table I above).

$$\overline{X}_n = 1/1-p \qquad D$$

$$\overline{M}_n = M_o \overline{XX}_n \qquad E$$

Based on these values, a crude estimate of the average number of polymer chains per vesicle is also possible. If it is assumed that (1) all of the vesicles are unilamellar, (2) the bilayer thickness is about 50 Å (A.D. Bangham et al., "Methods in Membrane Biology", E. D. Korn Editor; Plenum Press, New York., 1974, Volume 1, Page 1 et. seq.), and (3) each lipid occupies an area of 70 Å$^2$, then the calculated number of lipids per average vesicle of XX, XXI and XXII is about 2,000, 6,000, and 2,000, respectively. This estimate implies that, to a first approximation, polymerized vesicles of XX, XXI, and XXII bear an average of 80, 350, and 100 polymer chains, respectively.

Reductive Vesicle Depolymerization

The treatment of a polymerized vesicle dispersion of XX with 200 equivalents of dithiothreitol (DTT) for 1.5 hours at 50° C. led to about a 63% yield of regenerated monomer [quantitative thin layer chromatography (See Table II below)]. About 26% of the lipid remained at the origin. The $^1$H NMR and IR spectra of XX, isolated from the DTT-treated mixture, were identical to that found for the starting lipid. Using the more hydrophobic thiol reducing agent, 1-octanethiol (OT), the percentage of regenerated monomer was 67%, with only about 7% of the lipid remaining at the origin. Qualitative inspection of the thin layer chromatographic plates indicated the presence of lipid components lying in the region between $R_f$=0.0 and 0.26. These products were presumed to be oligomeric in nature, and were not analyzed either quantitatively or qualitatively. Analogous results were obtained for the depolymerization of polymerized vesicles of XXI (Table II below). The lower quantity of lipid measured at the origin for polymerized dispersions of XX, and XXI using OT as a reducing agent, is a likely result of more efficient disulfide reduction due to a high local concentration of the lipophilic thiol in the hydrocarbon core of the bilayer. Under similar reaction conditions, polymerized vesicles of XXII were reduced to a greater extent with DTT than with OT (See Table II below). In this case, the greater efficacy of DTT can be accounted for in terms of (1) the greater accessibility of the disulfide groups to the aqueous phase, where a higher effective concentration of DTT should be present and (2) the greater reducing power of the dithiol (R. P. Szajewski et al. J.Am. Chem Soc., 1980, Volume 102, Page 102 et seq. 2011; and W. W. Cleland, Biochemistry, 1964, Volume 3, Page 480 et seq.). Changes in apparent turbidity in all cases were minimal (less than 7%) after treatment with either DTT or OT. Gel filtration of depolymerized vesicles of XX and XXII (using DTT) indicated an 85% and 92% recovery, respectively, in the void volume of a Sepharose 6B column. Regenerated vesicles of XXI proved to be too unstable for Gel filtration.

TABLE II
Reductive Depolymerization of Phospholipid Vesicles

| Initial Monomer Composition of Structure | Reducing Agent | Regenerated Monomer[a] | Polymeric Lipid (%) |
|---|---|---|---|
| XX | DTT | 63 | 26 |
| XX | OT | 67 | 7 |
| XXI | DTT | 66 | 17 |
| XXI | OT | 85 | 5 |
| XXII | DTT | 93 | 9 |
| XXII | OT | 81 | 21 |

[a]Reductive depolymerization was carried out by adding (a) 200 equivalents of solid dithiothreitol (DTT) or (b) 200 equivalents of 1-octanethiol (OT) to the vesicle dispersion (0.75 mg of lipid in 0.5 mL of water), followed by brief shaking and heating (50° C., 1.5 hours). Turbidity changes in all cases were less than 7%. Depolymerization in 10 mM borate buffer (pH 8.5) and in pure water gave comparable results. Increasing the reaction time did not increase the yield of monomeric phospholipid. Phosphorus analysis was made for the following products: [$R_f$(XX)] = 0.26 ± 0.03; $R_f$(XXI) = 0.30 ± 0.03; $R_f$(XXII) = 0.30 ± 0.03. In each case, CHCl$_3$—CH$_3$OH—H$_2$O (65/25/4) was used as the solvent system. A control experiment indicated that about 90% of the phosphorus placed on a silica gel plate (in the form of oxidatively polymerized vesicles of XXII) was detected using procedures described below in the Experimental Procedures Section. Numbers reported are corrected values.

Thus the thiol containing lipids of the present invention are capable of yielding polymerizable-depolymerizable vesicle networks. The essential criterion for polymerization is that the oxidation process proceed via interlipid coupling. Based on the preferred conformation of phospholipids in the bilayer state, it appears that there is a predisposition toward interlipid coupling for the vesicles formed from the lipids of the present invention. Low-angle X-ray diffraction and NMR analysis indicate that for saturated phosphatidylcholines, the glycerol backbone is approximately perpendicular to the plane of the bilayer (P. B. Hitchcock et al. Proc. Natl. Acad. Sci. U.S.A. 1974, Volume 71, page 3036 et seq; P. B. Hitchcock et al., J. Mol. Biol, 1975, Volume 94, page 297 et seq.; R. A. Haberkorn et al., J. Am. Chem. Soc. 1977, Volume 99, page 7753 et seq; and P. L. Yeagle, Acc. Chem. Res., 1978, Volume 11, page 321 et seq.), where the two fatty acid chains extend unequally into the membrane. If a thiol group were positioned at identical carbon atoms in each of the A and B chains, the A chain thiol moiety should be in closer proximity to the center of the bilayer and the B chain thiol would lie closer to the inner and outer surface of the membrane. This segregation of thiol groups results in preferred interlipid coupling (E. Lopez et al. J. Am. Chem. Soc., 1982, Volume 104, page 305 et seq.). The fact that the disulfide bonds in these lipids can be reduced to the thiol state under mild conditions allows for the retention of an intact vesicle structure. Thus a redox-cycle may be used as the means for polymerizing and depolymerizing vesicles such as those comprised of one or more of XX, XXI and XXII.

Entrapment and Permeability

In order to measure the entrapment and permeability properties of the lipid membranes of the present invention, in the polymerized and nonpolymerized state, ($^{14}$C) sucrose was entrapped within the aqueous vesicle interiors using standard procedures. Table II (below) summarizes the results obtained. Nonpolymerized and polymerized vesicles of XX exhibited relatively small capture volumes (expressed as liters/mol) and moderate permeability. Vesicles of XXI showed a significantly larger capture volume in the polymerizable state, and similar permeability properties. Because of the inability of nonpolymerized vesicles of XXI to survive Gel filtration, corresponding entrapment and permeability measurements could not be made. Vesicles of XXII in the polymeric and monomeric form showed the highest capture volume and the lowest permeability. Within experimental error, polymerization of this XXII membrane (as well as vesicle membranes of XX) had no significant influence on its permeability. This insensitivity of membrane permeability toward polymerization is in contrast to polymethacrylate analogs previously reported (S. L. Regen et al. J.Am. Chem. Soc. 1980, Volume 102, page 6638 et seq; and S. L. Regen et al, Ibid, 1982, Volume 104, page 791 et seq.) and may be accounted for by the relatively low degree of polymerization obtained.

TABLE III

Vesicle Properties With Respect to Entrapment of and Permeability Toward Sucrose

| Vesicle Composition[a] | Entrapment (%) | Capture Volume (M$^{-1}$) | Retention (%) after 2 hours | Retention (%) after 4 hours |
|---|---|---|---|---|
| XX | 0.06 | 0.08 | 50 | 40 |
| P-XX | 0.07 | 0.09 | 58 | 33 |
| P-XXI | 0.10 | 0.54 | 61 | 13 |
| XXII | 0.74 | 1.06 | 72 | 56 |
| P-XXII | 0.72 | 1.05 | 75 | 58 |

[a]Dispersions were formed from 10 mg of phospholipid in 1.0 mL of 10 mM borate buffer (pH 8.4) containing 10 uCi of ($^{14}$C) sucrose. The Gel Filtration (Sephadex G-50-150) and dialysis (against 50 mL of pure water at 23° C.) procedures employed were similar to those previously described. (S. L. Regen, et al. supra) The prefix p refers to the polymerized state.

Phase-Transition Behavior

Changes in absorbance at 400 nm as a function of temperature were used to monitor phase transition behavior in the vesicular state. (P. N. Yi et al., Chem Phys. Lipids, 1973, Volume 11, page 114 et seq; T. Y. Tsong et al., Biochemistry, 1977, Volume 16, page 2674 et seq.; K. Kano et al. J. Am. Chem. Soc. 1979, Volume 101, page 4030 et seq.) A well-defined phase transition at about 22° C. was evident for nonpolymerized vesicles of XXII; subsequent polymerization of XXII did not alter this transition behavior. for vesicles of XXI (in the polymerized state) and XX (polymerized and nonpolymerized state) no apparent phase transitions were observed between 10° and 60° C. The well-defined transition for XXII is consistent with the fact that the polymer backbone is positioned near the head group. Nearly all of the hydrocarbon bilayer is, therefore, free to undergo cooperative disordering via the introduction of gauche rotational isomers (J. F. Nagle, Annu. Rev. Phys. Chem., 1980, Volume 31, Page 157 et. seg.). For the polymerized vesicles of XX and XXI, the backbone (running through the core of the bilayer) apparently restricts such structural reorganization. Similar differences in phase-transition behavior have previously been noted in polymerized methacryate-based phosphatidylcholine vesicles (A. Kusumi, et al., J. Am Chem. Soc. 1983, Volume 105, page 2975 et seq.)

Vesicle Stability

On standing at 25° C., nonpolymerized vesicles of XX remain stable for about 48 hours. After 72 hours, the dispersion shows a very substantial increase in turbidity. Oxidatively polymerized analogs of structure XX show no significant change in turbidity up to six days at 25° C. Beyond this period, however, there is substantial precipitation. Improvement in the shelf-life upon polymerization is also evident for vesicles formed from XXI and XXII. Here, constant turbidity is extended to 48 and 72 hours, from 4 to 10 hours, respectively. Polymerization, however, does not significantly improve the stability of these vesicles towards lysis using 0.6% sodium dodecylsulfate (SDS). In all such cases, the turbidity is decreased by about 50%. Qualitatively, therefore, disulfide-based polymerized vesicles of the type described hereinabove do not exhibit the extraordinary stability which has been found in polymerized vesicles derived from 1,2-bis[12-methacryloyloxy)dodecanoyl]-sn-glycero-3-phosphocholine. The latter show no evidence of disruption upon addition of up to 7% SDS. High vesicle stability is likely to be found only with crosslinked polymerized vesicle membranes. (R. L. Juliano et al., Biotechnology, 1984, page 882 et seq; and R. L. Juliano et al., Biochem. Biophys. Acta, 1984, Volume 774, page 109 et seq.)

The vesicles of the present invention it should be noted are still much more stable then prior art nonpolymerized liposomes used for drug delivery purposes, and are stable enough to be used for such purposes when used for such purposes when freshly made.

The shelf life stability of the disulfide containing vesicles of the present invention can be improved further by crosslinking them during the polymerization reaction involving the Structure I compounds. The crosslinking agents would include trimercaptan containing compounds such as trimercapto glycerides, of the structure

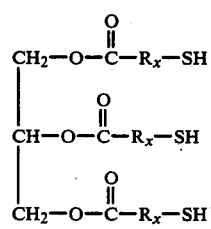

XXV wherein the $R_x$ groups may be the same or different and are saturated or unsaturated hydrocarbon radicals which may be alkyl, alkenyl, aryl, alkaryl or aralkyl. The $R_x$ alkyl or alkenyl groups may be linear, branched or cyclic. The SH groups can be located anywhere on the $R_x$ groups. The preferred of such $R_x$ groups or C10 to C25 linear or branched alkyl or alkenyl groups such as $(CH_2)_n$ and $CH$—$(CH_2)_n$—$CH_3$ wherein n is about 4 to 20 and preferably about 4 to 12. The more preferred of such structure XXV compounds are those in which all the $R_x$ groups are the same. The most preferred of the Structure XXV compounds are those in which the

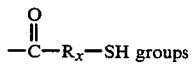
—C—$R_x$—SH groups have structures which are the same as those of Structures III and IV above.

The Structure XXV compounds are formed in a reaction D which is analogous to that of reaction A disclosed above, in that a disulfide compound of the structure

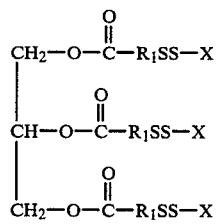  XXVI wherein, $R_1$ and X are as defined above, is reduced to form the Structure XXV compounds using the Reaction A conditions. The $R_1$ groups may be the same or different in the XXVI compounds. The structure XXVI compounds are formed from glycerol and disulfide compounds of Structure XII, and preferably those of Structures XIII and XIV.

The following examples are merely illustrative of the present invention and are not intended as a limitation upon the scope thereof.

General Methods

Unless stated otherwise, all chemicals and reagents were obtained commercially and used without further purification. Deionized water was distilled twice from $KMnO_4$. sn-glycero-3-phosphorylcholine (GPC) was prepared from egg lecithin (S. L. Regen et al, J. Amer. Chem. Soc., 1980, Volume 102, Page 6638 et seq, and by S. L. Regen, et al. supra, 1982, Volume 104, page 791 et seq.), and converted into its $CdCl_2$ complex (GPC—$CdCl_2$) using procedures similar to those described by J. S. Chadha, Chem. Phys. Lipids, 1970, Volume 4, page 104 et seq. ($^{14}C$)Sucrose (360 mCi/mmol, 20% ethanol solution) was obtained from ICN Laboratories. 11-Bromoundecanoic acid and 2-bromohexadecanoic acid were converted into 11-mercaptoundecanoic acid and 2-mercaptohexadecanoic acid, respectively (L. Rapoport et al., J. Amer. Chem. Soc., 1947, Volume 69, page 693 et seq., and E. Levine et al, J. Medicinal Chem, 1979, Volume 2, page 580 et seq.) 16-Bromohexadecanoic acid was similarly converted into its thiol derivative (Y. Kimura, et al., J. Org. Chem, 1983, Volume 48, Page 1533 et seq. and E. Levine, et al. supra.) Ethyl ethanethiosulfinate was prepared by oxidation of the corresponding disulfide (N. Furakawa, et al., J. Chem. Soc., Perkin II, 1980, page 432 et seq.). 5,5'-Dithio-bis(2-nitrobenzoic acid) (Ellman's Reagent) was purchased from Aldrich Chemical Co. and used directly. Dialysis experiments were carried out using Spectropor No. 6 dry membrane tubing (cylindrical diameter of 14.6 mm; M.W. cutoff 6000–8000) obtained from Spectrum Medical Industries. Vesicle dispersions were prepared either in pure water or in a 10 mM borate buffer (pH 8.5) containing 140 mM NaCl and 2 mM $NaN_3$. Chloroform used in depositing the phospholipids onto the walls of the glass tubes was HPLC-grade. Chloroform used for chromatography was reagent grade. Turbidity was determined by measuring the apparent Absorbance at 400 nm. $^1H$ NMR, IR and UV spectra were recorded on Varian EM 360L or a Bruker WM-250 MHz, Beckman Acculab 7 and Bausch & Lomb Spectronic 2000 spectrometers, respectively. Phase-transition measurements were carried out using a Perkin Elmer 320 spectrophotometer coupled with a digital temperature controller. Chromatographic separations were carried out using precoated Merck 0.25 mm silica gel 60 TLC plates (with fluorescent indicator) and Merck 70-230 ASTM silica gel) with the following eluting solvent mixtures: (A), 1% $CH_3OH$—$CHCl_3$; (B), $CHCl_3$—$CH_3$—$H_2O$ (4/5/1); (C), $CHCl_3$—$CH_3OH$—$H_2O$ (65/25/4); (D), $CHCl_3$—$CH_3OH$ (1/1). Unless stated otherwise, detection on TLC plates was made using iodine vapor or a UV lamp. Sonications were performed using a Heat Systems Model W-375 R bath type sonicator. Vortex mixing was carried out using a VWR Scientific mixer (Model K-550 G). Specific procedures used for electron microscopy and entrapment of and permeability toward ($^{14}C$)sucrose were similar to those previously described by S. L. Regen et al., J. Amer. Chem. Soc, 1980, Volume 102 and 1982, Volume 104, supra. Electron micrographs recorded using negative staining (2% uranyl acetate) were taken using a Philips 400 STEM microscope.

EXAMPLE 1

Preparation of 11-Ethyldithioundecanoic Acid
(Structure XIIA, m=10)

A mixture of 11-mercaptoundecanoic acid (1.40 g, 6.42 mmol), ethyl ethanethiosulfinate (1.18 g, 8.55 mmol) and triethylamine (0.72 mL, 5.2 mmol) in 16 mL of chloroform was stirred at room temperature for 24 hours. Evaporation of solvent under reduced pressure followed by chromatographic purification of the residue on a silica gel column (2.5×40 cm), eluting first with $CHCl_3$ and then solvent A, furnished 1.43 g (80%) of 11-ethyldithioundecanoic acid; $R_f$=0.52 (5% $CH_3OH$ in $CHCl_3$); IR(nujol) $\nu_{C=O}$ 1700 cm$^{-1}$; $^1H$ NMR($CDCl_3$) 1.3 (br s and t, 19H, $CH_2$ and $CH_3CH_2S$), 2.33 (t, 2H, $CH_2CO$), 2.45–2.9 (m, 4H, $CH_2S$), 11.7 (s, 1H, $CO_2H$).

EXAMPLE 2

Preparation of 16-Ethyldithiohexadecanoic Acid
(Structure XII A, $m_1$=15)

The procedures used for the synthesis of this structure XIIA compound were similar to those described for the preparation of the Structure XII A in Example 1 above. The isolated yield of product based on 16-mercaptohexadecanoic acid was 64%; $R_f$=0.52 (5% $CH_3OH$ in $CHCl_3$); IR(nujol) $\nu_{C=O}$ 1700 cm$^{-1}$; $^1H$ NMR ($CDCl_3$) 1.3 (br s and t, 29H, $CH_2$ and $CH_3CH_2$), 2.4 (t, 2H, $CH_2CO$), 2.5–2.9 (m, 4H, $CH_2S$), 10.9 (br s, 1H, $CO_2H$).

EXAMPLE 3

Preparation of 1,2-di(11-ethyldithioundecanoyl)-sn-glycero-3-phosphocholine (Structure VIIA, m=10)

To a mixture of GPC-CdCl$_2$ (89.6 mg, 0.196 mmol), 11-ethyldithioundecanoic acid (222 mg, 0.80 mmol) and 4-dimethylamino pyridine (48.0 mg, 0.40 mmol) dissolved in 2 mL of freshly distilled CHCl$_3$ was added 165 mg (0.80 mmol) of dicyclohexylcarbodiimide. The resulting mixture was then stirred for 48 hours at room temperature in the dark. After removal of solvent in vacuo, the residue was dissolved in a minimum volume of solvent B, and then applied to a 1.2×7 cm column of AG MP-50 resin (50–100 mesh, hydrogen form of a polystyrene based cationic exchange resin). Elution with 30 mL of solvent B followed by solvent evaporation and chromatographic purification using a 1×20 cm silica gel column, eluting with solvents D and C, respectively, afforded 139 mg (91%) of Structure VIIA, m=10, having an R$_f$=0.22, solvent C; IR $\nu_{C=O}$ 1720 cm$^{-1}$, $\nu_{N(CH_3)_3}$ 1090, 1050, 965 cm$^{-1}$; $^1$H NMR(CDCl$_3$) 1.3 (br s and t, 38H, CH$_3$CH$_2$S, and CH$_2$), 2.28 (m, 4H, CH$_2$CO), 2.5–2.9 (m, 8H, CH$_2$S), 3.36 (s, 9H, N(CH$_3$)$_3$), 3.65–4.5 (m, 8H, CH$_2$O and CH$_2$N), 5.15 (m, 1H, CHO).

EXAMPLE 4

Preparation of 1,2-di(16-ethyldithiohexadecanoyl)-sn-glycero-3-phosphocholine (Structure VII A, m$_1$=15)

The procedures used were similar to those described for the preparation of the compound of Structure VII A, in Example 3 above. The yield of the phospholipid, based on the starting carboxylic acid was 91%; R$_f$=0.30, solvent C; IR(nujol) $\nu_{C=O}$ 1749 cm$^{-1}$, $\nu_{N(CH_3)_3}$ 1090, 1050 and 970 cm$^{-1}$; $^1$H NMR (CDCl$_3$) δ1.21–1.4 (br s and t, 58H, CH$_2$ and CH$_3$CH$_2$S), 2.3 (t, 4H, CH$_2$CO), 2.5–2.8 (m, 8H, CH$_2$S), 3.35 (s, 9H, N(CH$_3$)$_3$), 5.15 (m, 1H, CHO).

EXAMPLE 5

Preparation of 1,2-di(11-mercaptoundecanoyl)-sn-glycero-3-phosphocholine (Structure XX)

To a solution of 87 mg (0.112 mmol) of Structure VIIA, m=10, prepared as in Example 3, dissolved in 1 mL of ethanol plus 1 mL of water, was added 0.11 mL (0.45 mmol) of tri-n-butylphosphine. After stirring the mixture at room temperature for 11 hours (in the dark), the solvent was then evaporated under reduced pressure and the residue purified by column chromatography on silica gel (1×20 cm), eluting with solvent D and C, successively. The phospholipid product (70 mg, 95%), showed a single spot by TLC, having an R$_f$ equalling 0.26 (solvent C); IR(neat) $\nu_{C=O}$ 1730 cm$^{-1}$, $\nu_{N(CH_3)_3}$ 1090, 1060, 970 cm$^{-1}$; $^1$H NMR(CDCl$_3$) 1.27 (br s, 32H, CH$_2$), 2.0–2.75 (m, 8H, HSCH$_2$ and CH$_2$CO), 3.35 (s, 9H, N(CH$_3$)$_3$); 3.65–4.5 (m, 8H, CH$_2$O and CH$_2$N), 5.15 (m, 1H, CHO). Calculated for Structure XX, C$_{30}$H$_{60}$O$_8$NS$_2$P: N, 2.13; S, 9.75; P, 4.71. Found: N, 1.92; S, 8.38; P, 4.87.

EXAMPLE 6

Preparation of 1,2-di(16-mercaptohexadecanoyl)-sn-glycero-3-phosphocholine (Structure XXI)

The procedures used were similar to those used for the preparation of Structure XX, described in Example 5 above; starting with 16-mercapto palmitic acid as the compound of Structure XVI A, and proceding through Reactions C, B and A respectively; the isolated yield of Structure XXI was 98%; R$_f$=0.30, solvent C; IR(nujol) $\nu_{C=O}$ 1730 cm$^{-1}$, $\nu_{N(CH_3)_3}$ 1090, 1060 and 970 cm$^{-1}$; $^1$H NMR(CDCl$_3$)δ, 1.3 (br, s, 52, H CH$_2$), 2.1–2.7 (m, 10H, CH$_2$CO, CH$_2$S, SH), 3.4 (s, 9H, N(CH$_3$)$_3$), 3.7–4.3 (m, 8H, CH$_2$O, CH$_2$N), 5.15 (m, 1H, CHO). Calculated for Structure XXI, C$_{40}$H$_{80}$O$_8$PNS$_2$: N, 1.76; S, 8.03; P, 3.88. Found: N, 1.95; S, 6.35; P, 4.08.

EXAMPLE 7

Preparation of 2-Ethyldithiohexadecanoic Acid (Structure XII B, m$_1$=13)

Procedures used for the synthesis of this Structure XII B compound were similar to those described above for the preparation of Structure XIIA in Example 1. The isolated yield of this Structure XIIB product, based on 2-mercaptohexadecanoic acid, was 72%; R$_f$=0.63 (5%, CH$_3$OH in CHCl$_3$; IR(nujol) $\nu_{C=O}$ 1700 cm$^{-1}$; $^1$H NMR(CDCl$_3$) 0.9 (t, 3H, CH$_2$CH$_3$), 1.2–1.3 (br s, 29H, CH$_2$ and CH$_3$CH$_2$S), 2.4–2.5 (q, 2H, CH$_3$CH$_2$S), 3.2–3.3 (t, 1H, CHS), 10.5 (s, 1H, CO$_2$H).

EXAMPLE 8

Preparation of 1,2-di(2-ethyldithiohexadecanoyl)-sn-glycero-3-phosphocholine, Structure VIIB, m$_1$=13, The procedures used were similar to those used for the preparation of Structure XX described above using Structure XIIB, m$_1$=13, as prepared in Example 7, in Reaction B. The isolated yield of Structure VIIB was 82%; R$_f$=0.30, solvent C; IR(nujol) $\nu_{C=O}$ 1725 cm$^{-1}$ $\nu_{N(CH_3)_3}$ 1090, 1060, 965 cm$^{-1}$; $^1$H NMR (CDCl$_3$)δ 0.9 (t, 6H, CH$_3$CH$_2$), 1.2–1.3 (br s and t, 58H, CH$_2$, CH$_3$CH$_2$S), 2.4–2.5 (q, 4H, CH$_3$CH$_2$S), 3.2–3.4 (br s, 11H, N(CH$_3$)$_3$ and CHS), 3.7–4.5 (m, 8H, CH$_2$O, CH$_2$N), 5.15 (m, 1H, CHO).

EXAMPLE 9

Preparation of 1,2-di(2-mercaptohexadecanoyl)-sn-glycero-3-phosphocholine, Structure XXII The procedures used were similar to those used for the preparation of Structure XX described above starting with 1-mercapto palmitic acid as the compound of Structure XVIB and proceeding through reactions C, B and A respectively. The isolated yield of Structure XXII was 76%; R$_f$=0.30, solvent C; IR(nujol) $\nu_{C=O}$ 1725 cm$^{-1}$; N(CH$_3$)$_3$ 1090, 1060 and 970 cm$^{-1}$; $^1$H NMR (CDCl$_3$)δ 0.9 (t, 6H, CH$_3$CH$_2$), 1.2–1.3 (br s and t, 52H CH$_2$ and CH$_3$CH$_2$S), 2.2 (br s, 2H, SH), 3.2–3.4 (br s, 11H, N(CH$_3$)$_3$ and CHS), 3.7–4.5 (m, 8H, CH$_2$O and CH$_2$N), 5.2 (m, 1H, CHO). Calculated for XXII, C$_{40}$H$_{80}$O$_8$PNS$_2$: N, 1.76; S, 8.03; P 3.88. Found: N, 1.71; S, 6.88; P, 4.22.

EXAMPLE 10

The preparation of Cyclized Monomer of Structure XXIII

Phospholipid of structure XX (20 mg, 0.03 mmol) was dissolved in 40 mL of benzene containing 8.54 uL (0.06 mmol) of triethylamine. A solution of 7.84 mg (0.03 mmol) of iodine dissolved in 20 mL of benzene was then added dropwise over a period of 1 hour. The combined mixture was stirred for 5 hours at room temperature, and then washed successively with 5% sodium thiosulfate and distilled water. The organic layer was dried over sodium sulfate, concentrated, and the crude product purified by chromatography (silica gel) using a gradient of $CHCl_3$, and solvents D and C, to give 50 mg (25%) of Structure XXIII. $R_f=0.25$, solvent D; IR(nujol) $\nu_{C=O}$ 1725 cm$^{-1}$ $\nu_{N(CH_3)_3}$ 1090, 1065, 965 cm$^{-1}$; $^1$H NMR (CDCl$_3$)$\delta$ 1.3 (br s, 32H, CH$_2$), 2.3 (m, 4H, CH$_2$C=O), 2.5–2.7 (m, 4H, CH$_2$S), 3.4 (s, 9H, N(CH$_3$)$_3$), 3.7–4.5 (m, 8H, CH$_2$O and CH$_2$N$^+$), 5.2 (m, 1H, CHO); Fast Atom Bombardment, MH$^+$ m/z=656.

EXAMPLES 11 TO 13

Vesicle Preparation

Typically, 2.0 mg (0.003 mmol) of a lipid, such as that of Structures XX, XXI and XXII, dissolved in 0.1 mL of HPLC-grade chloroform, was placed in a ½"×4" test tube and the solvent slowly evaporated with the aid of a stream of nitrogen. The tube was then evaporated (18 hours, 22° C. (1.0 mm), sealed with a No-Air stopper, and flushed with a stream of nitrogen. A borate buffer (2 mL) containing 140 mM NaCl and 2 mM NaN$_3$ (pH 8.5) was added to this tube via syringe and the tube then placed in a water bath (50° C.) for 10 minutes. A multilamellar dispersion was then formed by vigorous vortex-milling for 2 minutes. Subsequent sonication in a bath type sonicator at 50° C. for 1 hour produced a clear stable dispersion whose optical density remained constant upon further sonication. Thin layer chromatography on silica gel (solvent C) indicated that no liquid decomposition occurred; i.e., a single spot was observed, having an $R_f$=0.26 for a vesicle formed from Structure XX
$R_f$=0.30 for a vesicle formed from Structure XXI
$R_f$=0.30 for a vesicle formed from Structure XXII

EXAMPLES 14 TO 16

Vesicle Polymerization

Typically, 7 μL of 30% H$_2$O$_2$ (20 equiv) was added to a 1.0 mL dispersion of one Structures XX, XXI or XXII containing 2.0 mg of lipid, and the resulting dispersion was heated under a nitrogen atmosphere for 3 hours at 40° C. Thin layer chromatography showed a single spot at the origin (iodine). The dispersion was then dialyzed against 100 mL of doubly distilled water for 18 hours at room temperature in order to remove excess hydrogen peroxide. Quantitative analysis for thiol content indicated that the following amounts of thiol groups remained for the respective polymers:

| Polymer of Vesicle | % Thiol groups remaining, about |
|---|---|
| XX | 4 |
| XXI | 6 |
| XXII | 5 |

EXAMPLES 17 TO 19

Vesicle Depolymerization

Typically, a 1.0 mL polymerized dispersion of a structure XX, XXI or XXII (2.9 mg of lipid) that had been dialyzed to remove excess hydrogen peroxide, was purged with a stream of nitrogen, and mixed with 60 mg (0.388 mmol) of dithiothreitol. The resulting dispersion was purged with nitrogen for 5 minutes, and heated in a water bath for 1.5 hours at 50° C. Qualitative analysis by TLC indicated substantial regeneration of each of the Structure XX, XXI and XXII lipids respectively, using Solvent C, and each gave positive thiol tests, with the observed $R_f$ and quantitative phosphorous analyses for such lipids indicating the following yields of regenerated lipid

| Lipid | $R_f$ | % Yield of Regenerated Lipid |
|---|---|---|
| XX | 0.26 | 63 |
| XXI | 0.30 | 66 |
| XXII | 0.30 | 93 |

EXAMPLE 20

Preparation of tris-(11-ethyldithioundecanoyl)glyceride-XXVII (Structure XXVI, wherein each $R_1$ is $(CH_2)_{10}$ and each X is ethyl)

A mixture of 0.074 g (0.80 mmol of glycerol, 0.294 g (2.41 mmol) of 4-dimethylaminopyridine, 0.992 g (4.8 mmol) of dicyclohexylcarbodiimide, 1.34 g (4.8 mmol) of 11-ethyldithioundecanoic acid and 40 mL of freshly distilled chloroform was stirred for 12 hours at room temperature under a nitrogen atmosphere. The solvent was then removed under reduced pressure and the triglyceride dissolved in hexane—chloroform (1/1). The insoluble residue was triturated with hexane—chloform, and the solubilized fraction combined with the triglyceride solution, and then concentrated under reduced pressure. The crude product was then dissolved in a minimum volume of chloroform and purified on a silica gel column, using chloroform as the eluting solvent, affording 0.60 g (95%) of XXVII; $R_f$=0.5, hexane—ethyl acetate (8/2); $^1$H NMR (CDCL$_3$) 1.2–1.3 (br s and t, 57H, CH$_2$ and CH$_3$CH$_2$), 2.05–2.85 (br s and t, 18H, CH$_2$Co and CH$_2$S), 4.2 (q, 4H, CH$_2$O), 5.2 (m, 1H, CHO).

EXAMPLE 21

Preparation of tris-(11 mercaptoundecanoyl)glyceride-XXVIII (Structure XXV, wherein each $R_x$ is $(CH_2)_{10}$)

A solution comprised of 0.093 g (0.046 mmol) of tri-n-butylphosphine dissolved in 3.1 mL of ethanol was purged with a stream of nitrogen and added to 0.066 g (0.075 mmol) of XXVII. After stirring the mixture under a nitrogen atmosphere for 3 hours, the solvent was removed under reduced pressure. The residue was purified by chromatography on a silica gel column using hexane—ethyl acetate (8/2) as the eluent, affording 0.042 g (81%) of XXVIII; $R_f$=0.6, hexane—ethyl acetate (8/2); IR(KBr) $\nu_{C=O}$ 1736 cm$^{-1}$; $^1$H NMR (CDCL$_3$) 1.2–1.3 (br s, 51H, CH$_2$ and SH), 2.15–2.55 (m, 12H, CH$_2$CO and CH$_2$SH), 4.2 (q, 4H, CH$_2$O), 5.2 (m, 1H, CHO).

Calculated for XXVIII, $C_{36}H_{68}S_3O_6$: C, 62.43; H, 9.82; S, 13.87. Found: C, 62.69; H, 10.09; S, 13.65.

Other Analytical/Experimental Procedures that were Employed

Thiol Analysis

A 0.2M Tris buffer (pH 8.2) was prepared from tris(-hydroxymethylamino)methane and its hydrochloride salt, and subsequently diluted with an equal volume of absolute ethanol (containing 1% EDTA). To 10 mL of the resulting buffer was added 40 mg (0.101 mmol) of 5,5'-dithio-bis(2-nitrobenzoic acid) (DTNB reagent solution). For thiol analysis, 0.040 mL Of a given vesicle dispersion was added to 1.5 mL of the above buffer solution (containing ethanol and EDTA) plus 0.1 mL of the DTNB reagent solution, and the Absorbance at 412 nm measured after 20 minutes at room temperature. [(A.F.S.A. Habeen, "Methods in Enzymology, Volume 25, C.H.W. Hirs et al., Eds. Academic Press, N.Y., 1972, Page 457 et seq.].

Phosphorous Analysis

Procedures used for the determination of phosphorus were similar to those previously described by S. L. Regen, et al., Macromolecules, 1983, Volume 16, Page 335 et seq.

Qualitative Thin Layer Chromatography

Vesicle dispersions (before and after polymerization) were spotted on a TLC plate, dried under a stream of nitrogen and developed with solvent C. Product were detected either by iodine vapor or by spraying the plate with 0.1% of DTNB in the Tris buffer described (containing ethanol and EDTA).

Quantitative Thin Layer Chromatography

After qualitative thin layer chromatographic analysis was made (iodine detection), silica gel plates (5×15 cm) containing adsorbed lipid was removed from appropriate zones and analyzed directly for phosphorus content. Procedures used were similar to those previously described by S. L. Regen, et al., Macromolecules, 1983, Volume 16, Page 335 et seg., except a larger volume of magnesium nitrate solution (about 0.20 mL) was employed, and the derivatized mixture was filtered to remove silica gel prior to UV analysis.

As noted above Structure I compounds containing phosphine choline groups as the head group, instead of phosphate choline groups, may also be used in the present invention. Such compounds would have the structure

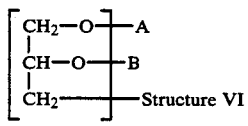  XXIX wherein A, B, and Structure VI are as defined above.

The Structure XXIX compounds may be prepared by first reacting glycerol with phosphinic acid, and by then introducing the A and B groups as otherwise disclosed above.

The compounds of Structure XXIX and those of Structure I may also be depicted by the following more generic structure

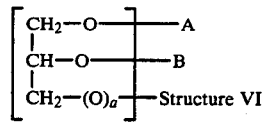  XXX wherein A, B and Structure VI are as defined above, and a is 0 or 1. When a is 0 the compound is that of Structure XXIX and when a is 1 the compound is that of Structure I.

Similarly the compounds of Structure XXIV and the cyclic analogues of Structure XXIX may be more generically depicted by the structure

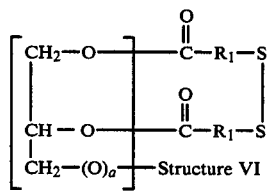

wherein a is 0 or 1 and $R_1$ and Structure VI is as defined above.

What is claimed is:

1. A compound of the structure

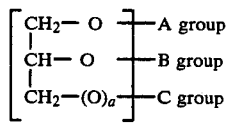

wherein a is 0 or 1,
one of said A, B and C groups is a liposome forming head group adaptable to forming vesicles, one or two of the remaining of such A, B and C groups have the structure

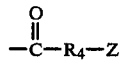

wherein Z is SH or $SSR_5$, $R_4$ is a hydrocarbon radical containing about 10 to 25 carbon atoms, $R_5$ is a $C_1$ to $C_{25}$ hydrocarbon radical and the remainder, if any, of such A, B and C groups is an inert group.

2. A compound as in claim 1 wherein said head group has the structure

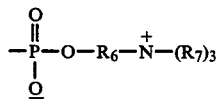

wherein $R_6$ and $R_7$ are $C_1$ to $C_4$ hydrocarbon radicals.

3. A compound as in claim 2 wherein said head group has the structure

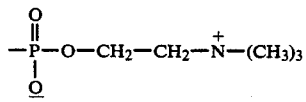

4. A compound as in claim 2 wherein a is 1.

5. A compound as in claim 2 wherein a is 0.

6. A compound as in claim 1 wherein said head group is selected from the group consisting of phosphatidyl choline, phosphatidyl alkanol amines, phosphatidyl glycerol and pharmaceutically acceptable salts thereof.

7. A compound as in claim 6 wherein said head group is a phosphatidyl choline group.

8. A compound as in claim 1 wherein Z is SH.

9. A compound as in claim 8 wherein one or two of the A, B and C groups have the structure

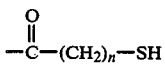

wherein n is about 10 to 25.

10. A compound as in claim 9 wherein n is about 10.

11. A compound as in claim 9 wherein n is about 15.

12. A compound as in claim 8 wherein one or two of the A, B and C groups have the structure

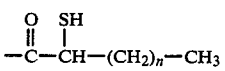

wherein n is about 8 to 10.

13. A compound as in claim 12 wherein n is about 13.

14. A compound as in claim 1 wherein Z is $SSR_5$.

15. A compound as in claim 14 wherein one or two of the A, B and C groups have the structure

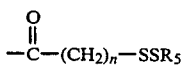

wherein n is about 10 to 25.

16. A compound as in claim 15 wherein n is about 10.

17. A compound as in claim 15 wherein n is about 15.

18. A compound as in claim 14 wherein one or two of the A, B and C groups have the structure

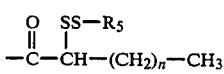

wherein n is about 8 to 10.

19. A compound as in claim 18 wherein n is about 13.

20. A vesicle formed from a compound of claim 1.

21. A vesicle formed from a compound of claim 2.

22. A vesicle formed from a compound of claim 4.

23. A vesicle formed from a compound of claim 6.

24. A compound as in claim 5 wherein said head group is a phosphine choline group or a pharmaceutically acceptable salt thereof.

* * * * *